United States Patent [19]

Mueller et al.

[11] Patent Number: 5,010,194

[45] Date of Patent: Apr. 23, 1991

[54] METHOD FOR THE RESOLUTION OF FOLINIC ACID

[75] Inventors: Hans R. Mueller, Schaffhausen; Martin Ulmann, Dachsen; Josef Conti, Schaffhausen, all of Switzerland; Guenter Muerdel, Tengen-Buesslingen, Fed. Rep. of Germany

[73] Assignee: Eprova AG, Schaffhausen, Switzerland

[21] Appl. No.: 432,819

[22] Filed: Nov. 7, 1989

[30] Foreign Application Priority Data

Nov. 11, 1988 [CH] Switzerland ............ 04182/88

[51] Int. Cl.$^5$ .......................................... C07D 475/04
[52] U.S. Cl. ........................................... 544/258
[58] Field of Search ................................ 544/258

[56] References Cited

U.S. PATENT DOCUMENTS

| 2,688,018 | 8/1954 | Cosulich | 544/258 |
|---|---|---|---|
| 4,148,999 | 4/1979 | Temple et al. | 544/258 |
| 4,500,711 | 2/1985 | Wisowaty | 544/258 |
| 4,959,472 | 9/1990 | Wood et al. | 544/258 |

FOREIGN PATENT DOCUMENTS

| 0266042 | 5/1988 | European Pat. Off. | 544/258 |
|---|---|---|---|
| 305574 | 2/1955 | France . | |
| 649550 | 5/1985 | Switzerland . | |
| WO88/08844 | 11/1988 | World Int. Prop. O. . | |

OTHER PUBLICATIONS

Mueller et al., Chem. Abstr., vol. 111, entry 102722q (1988), abstracting WO 88 08 844.
Chem. Abstr. vol. 98, entry 215624r (1983).
Straw et al, Cancer Res., vol. 44, pp. 3114-3119 (1984).
Swiss Confederation Federal Bureau of Intellectual Property Disclosure of Invention, published May 2, 1955, No. 305574, Class 116h, Appln. filed May 3, 1952, "Process for the Preparation of Calcium 5-Formyl-5,6,7,8-Tetrahydropteroylglutamate."
Temple et al., Jour. Med. Chem. 1979, vol. 22, No. 6, pp. 731-734.
Chem. Abstracts, vol. 107, entry 214060w (1987).
Merck Index, 10th Edition (1983), Entry 4111.
Russian Article: Kaplan et al., Biologiceskie Nauki, vol. 7, pp. 22-37 (1987).
Fontecilla-Camps et al., *Chemistry and Biology of Pteridines*, p. 235, Elsevier/North-Holland, NY.
J. Feeney, Biochemistry, vol. 20, pp. 1837-1842 (1981).
Cosulich, J. Am. Chem. Soc., vol. 74, pp. 4215-4216 (1952).
J. Am. Chem. Soc., vol. 101:20, pp. 6114-6115 (Sep. 26, 1979).
Rees et al., "A Simple and Effective Method for the Preparation of 6(R)-and 6(S)-Diastereoisomers," J. Chem. Soc., Chem. Commun., pp. 470-472 (1987).
Rees et al., Tetrahedron, vol. 42, No. 1, pp. 117-137 (1986).
Kaufman et al., The Journal of Biological Chemistry, vol. 238, No. 4, pp. 1498-1500 (Apr. 1963).
White et al., The Journal of Biological Chemistry, vol. 253, No. 1, pp. 242-245 (Jan. 10, 1978).
Fachlexikon ABC Chemie, Stereoisomeric, p. 1077 (1987).
Rowe, Analytical Biochemistry 22, pp. 166-177 (1968).
Choi et al., Analytical Biochemistry 168, pp. 398-404 (1988).
Folates and Pterins, vol. 1, Chemistry and Biochemistry of Folates, pp. xiii and 99 (1984).
Kalbermattan et al., Helvitica Chemica Acta, vol. 64, Fasc. 8, Nr. 266, p. 2627 (1981).

*Primary Examiner*—Donald G. Daus
*Attorney, Agent, or Firm*—Millen, White & Zelano

[57] ABSTRACT

A method for the resolution of (6R,S)-folinates into their diastereomers, comprising adding a water-soluble alkali metal, ammonium or alkaline earth metal salt of an inorganic or organic acid to an aqueous solution of a salt of (6R,S)-folinic acid, removing by filtration the salt which separates out, which consists predominantly of the corresponding (6R)-folinates, and isolating the desired (6S)-folinate from the filtrate.

21 Claims, No Drawings

METHOD FOR THE RESOLUTION OF FOLINIC ACID

CROSS-REFERENCE TO RELATED APPLICATION

This application is related to U.S. Application Ser. No. 07/294,631, filed Dec. 23, 1988.

BACKGROUND OF THE INVENTION

The invention relates to a method for the resolution of N-5-formyl-(6R,S)-5,6,7,8-tetrahydrofolic acid (5-CHO-(6R,S)-THF), called folinic acid for short, and isolation of N5-formyl-(6S)-5,6,7,8-tetrahydrofolic acid (also named as 5-CHO-(6,S)-THF), the biochemically active citrovorum factor (=growth factor for Leuconostoc citrovorum).

Folinic acid contains 2 centers of asymmetry. In this connection, because folinic acid is synthesized from folic acid, N-(pteroyl)-L-glutamic acid, the optically active C atom contained in the glutamic acid residue is in the L form, whereas the optically active C atom in position 6, which has been produced by hydrogenation of the double bond in the 5,6-position of the pteroyl radical, is in the racemic, the (6R,S), form. Synthetic folinic acid (=leucovorin) accordingly consists of a 1:1 mixture of two diastereomers.

The naturally occurring, e.g., in the liver, folinic acid is solely in the (6S) form as 5-CHO-(6S)-THF. 5-CHO-(6R,S)-THF (folinic acid) is used in the form of its calcium salt (leucovorin calcium) as a pharmaceutical for the treatment of megaloblastic folic acid deficiency anemia, as an antidote for enhancing the tolerability of folic acid antagonists, specifically of aminopterin, methotrexate and fluorouracil, in cancer therapy (leucovorin rescue) and for the treatment of autoimmune diseases such as psoriasis and rheumatoid arthritis, as well as for enhancing the tolerability of certain antiparasitics, for example trimethoprim-sulfamethoxazole, in chemotherapy. After administration of 5-CHO-(6R,S)-THF, the (6S) content of this diastereomer mixture is rapidly converted into 5-Me-(6S)-THF, whereas the (6R) content is not metabolized and is slowly excreted with the urine: J.A. Straw et al., Cancer Research 44, 3114–3119 (1984).

F.M. Sirotnak et al., Biochemical Pharmacology 28, 2993–97 (1979) have found that the efficacy at suppressing the inhibition of cell growth of methotrexate in L 1210 cultures of the unnatural diastereomer of folinic acid [5-CHO-(6R)-THF] is a 100th, and of the chemically synthesized diastereomer mixture [5-CHO-(6R,S)-THF] is one half that of the natural diastereomer [5-CHO-(6S)-THF]. C. Temple et al., Cancer Treatment Reports 65, 1117–9 (1981), have produced in vivo confirmation of these results obtained in vitro and have found that the natural diastereomer is more than twice as effective as the mixture of diastereomers [leucovorin] with regard to reducing the toxicity of methotrexate. These authors in fact suggested that the unnatural diastereomer may have an injurious effect.

This is because 5-CHO-(6R)-THF inhibits some enzymes responsible for $C_1$ transfer and thus inhibits the biochemical action of tetrahydrofolates: R.P. Leary et al., Biochem. Biophys. Res. Commun. 56. 484 (1973); V.F. Scott et al., ibid. 14, 523 (1964); G.K. Smith et al., Biochemistry, 20, 4034 (1981). The use of (6S)-tetrahydrofolates in place of (6R,S)-tetrahydrofolates ought not only to be twice as effective but also to have qualitative therapeutic advantages.

Hence, there is a need to replace the 1:1 mixture of diastereomers which has hitherto been used by the natural active substance [5-CHO-(6S)-THF].

Several attempts have been made to resolve 5-CHO-(6R,S)-THF and to carry out the asymmetric synthesis of 5-CHO-(6S)-THF. D. Cosulich et al., J. Amer. Chem. Soc. 74, 4215–16 (1952), U.S. Pat. No. 2,688,018 (Aug. 31, 1954) have attempted, for example, to bring about the resolution by fractional crystallization of an alkaline earth metal salt, for example, the calcium or strontium salt, of 5-CHO-(6R,S)-THF from aqueous solutions [see also J.C. Fontecilla-Camps et al., J. Amer. Chem. Soc. 101, 6114 (1979)].

However, the desired resolution cannot be achieved under the conditions published by D. Cosulich et al. On crystallization of, for example, the calcium salt of 5-CHO-(6R,S)-THF from water at pH 7–8 it is always the 6R,S form which is recovered, as can be demonstrated quantitatively by means of chromatographic analysis on a chiral HPLC column and on the basis of the optical rotation. It is immaterial in this connection whether crude or pure calcium salt of 5-CHO-(6R,S)-THF is used for the crystallization; the (6R,S) form is always recovered. Nor is it possible to achieve resolution and enrichment of the (6S) form by seeding the supersaturated aqueous solution of an alkaline earth metal salt of 5-CHO-(6R,S)-THF with authentic alkaline earth metal salt of 5-CHO-(6S)-THF.

Resolution of the pair of diastereomers has also been attempted by chromatography: J. Feeney et al., Biochemistry 20, 1837 (1981). In addition, the (6S)-isomers have been prepared by stereospecific reduction of dihydrofolates in the presence of dihydrofolate reductase: L. Rees et al., Tetrahedron 42, 117 (1986).

L. Rees et al., J. Chem. Soc., Chem. Commun. 1987, 470, EP-A2 0,266,042 have described a method for resolving (6R,S)-THF, with the aid of which it was possible to produce small amounts of 5-CHO-(6S)-THF and 5-CHO-(6R)-THF. The method comprises reacting (6R,S)-THF with (-)-menthyl chloroformate to give the diastereomeric 5-(-)-menthyloxycarbonyl-tetrahydrofolic acids, resolving the latter by repeated treatment with n-butanol, heating the resulting diastereomers with a saturated solution of hydrogen bromide in a mixture of formic acid and acetic acid, when 5-formyl-(6S)- and (6R)-THF are formed after hydrolysis, and finally isolating the latter as calcium salts. This method is laborious and difficult and requires highly toxic phosgene for the preparation of the chiral reagent. In addition, the starting material (6R,S)-THF is very unstable. On elimination of the chiral auxiliary group with HBr in AcOH at >50° C., there is partial elimination of glutamic acid, resulting in byproducts which can be separated off only with difficulty. The (6S)-folinic acid produced by a method of this type would be so costly that scarcely any consideration would be given to using it in place of (R,S)-tetrahydrofolates.

Thus, the above-described prior art does not disclose any technically and economically attractive method for obtaining (6S)-tetrahydrofolates.

SUMMARY OF THE INVENTION

It is an object of one aspect of the present invention to provide a straight-forward and industrially applicable process for preparing 5-CHO-(6S)-THF, free or substantially free from the 6-diastereomer thereof.

Upon further study of the specification and appended claims, further objects and advantages of this invention will become apparent to those skilled in the art.

To attain such objects, there is provided a method for the resolution of (6R,S)-folinates (hereinafter the term 5-CHO-THF), comprising adding a sufficient amount of a water-soluble alkali metal, ammonium or alkaline earth metal salt of an inorganic or organic acid to an aqueous solution of a salt of (6R,S)-folinic acid to form a precipitate of a salt of (6R)-folinic acid, separating off, e.g., by filtration, the resultant (6R)-folinate precipitate, and isolating the (6S)-folinate from the filtrate, and to the individual steps thereof.

This invention particularly provides substantially pure 5-CHO-(6S)-folinate, or a salt thereof.

It has now been found, surprisingly, that after addition of water-soluble alkali metal, ammonium or alkaline earth metal salts of inorganic or organic acids to aqueous solutions of salts of (6R,S)-folinic acid [5-CHO-(6R,S)-THF] the corresponding folinate which consists very predominantly of the unnatural diastereomer (6R)-folinate [5-CHO-(6R)-THF] separates out. The latter can be removed by filtration. It is possible to isolate from the filtrate, which predominantly consists of the desired natural (6S)-folinate, the (6S)-folinate by addition of a water-miscible organic solvent such as, for example, ethanol or acetone and/or of a water-soluble alkaline earth metal salt. Residues of (6R)-folinate can subsequently be removed from the (6S)-folinate by recrystallization.

By "ammonium salt" are meant here and hereinafter ammonium salts which are unsubstituted or substituted 1 to 4 times, including the pyrrolidinium, piperidinium and morpholinium salts. Particularly suitable substituents are alkyl or hydroxyalkyl groups having 1 to 4 C atoms or benzyl.

The resolution of alkaline earth metal salts of (6R,S)-folinates by this method of first precipitating out 6R-folinate is applicable only at an approximately neutral pH, e.g., a pH of 6 to 8, preferably 7 to 8. In contrast, the product which initially precipitates out of an alkaline medium (pH>8) consists, in agreement with the method described in PCT/EP Patent Application 88/00341 (published on Nov. 17, 1988, as WO 88/08844), predominantly of alkaline earth metal (6S)-folinate. Conversely, on resolution of alkali metal (6R,S)-folinates the (6R)-folinate initially separates out after addition of alkali metal halides either from an approximately neutral or from an alkaline medium.

It is unnecessary and, in general, not expedient for the cations in the mixture of diastereomers which is to be resolved and those of the added alkali metal, ammonium or alkaline earth metal salts of an inorganic or low organic acid to be the same. If, for example, a water-soluble alkali metal halide, for example sodium iodide, is added to a solution of an alkaline earth metal salt of (6R,S)-folinate at approximately neutral pH, the corresponding alkaline earth metal (6R)-folinate initially precipitates out. The outcome is similar when a water-soluble alkaline earth metal salt is added to a solution of an alkali metal (6R,S)-folinate at approximately neutral pH. The corresponding alkaline earth metal (6R)-folinate initially precipitates out. When soluble alkali metal salts of inorganic acids are added to a solution of alkali metal (6R,S)-folinate the corresponding alkali metal (6R)-folinate initially precipitates out, occasionally only after addition of an organic solvent such as methanol, ethanol, isopropanol or acetone.

After the precipitated (6R)-folinate is removed from the mother liquor, the alkali metal (6S)-folinate can be induced to separate out of the mother liquor by addition of (more) organic solvent. However, it is also possible to bring about the separation out of the corresponding alkaline earth metal (6S)-folinate from the mother liquor by the addition of water-soluble alkaline earth metal salts. No problems are caused if the pH of the solution rises to >8 during this.

The requisite amount of water-soluble alkali metal or ammonium salts of organic or inorganic acids must be sufficient to effect precipitation of the (6R) folinate. It is generally about 0.5 to 10 times, preferably 1 to 5 times, the amount by weight relative to the weight of (6R,S)-folinate used. Water-soluble alkaline earth metal salts are required in far smaller amounts.

Preferred operating temperatures for each step are as follows: forming the (6R) folinate precipitated: −5 to 50, more preferably 0° to 25° C.; for the isolation of the (6S) folinate from the filtrate: −5 to 50 more preferably, 0° to 25° C. As for the times involved, the time for precipitating the (6R) folinate is sufficient to form a precipiate, for example, 3 to ∼70 hours, depending on the operating conditions. The time for precipitating the (6S)-folinate is also sufficient to form a precipitate, for example, 3 to ∼70 hours, depending on the operating conditions.

The often cited method of D. Cosulich et al could never be reproduced by subsequent scientits because e.g. pure calcium (6S)-folinate is more soluble in water than calcium (6R)-folinate and calcium (6R,S)-folinate:

| Compound | Solubility in water in % w/w | |
|---|---|---|
| | at 0° C. | 20° C. |
| calcium-(6S)-folinate | 1.9 | 2.2 |
| calcium-(6R)-folinate | 1.7 | 1.7 |
| calcium-(6R,S)-folinate | 0.63 | 1.2 |

The separation of the diastereoisomers is further complicated by the strong tendency of aqueous solutions of folinates to form supersaturated solutions. This tendency increases with decreasing purity of the compounds. It is greater with (6R)-folinates than with (6S)-folinates.

When optimal conditions, which can be routinely established, are maintained, the (6R)-folinate separates out in virtually optically pure form and in high yield. Under such conditions the mother liquor in each case now contains only minor amounts of (6R)-folinate and, accordingly, the (6S)-folinate which is subsequently induced to separate out, for example by addition of organic solvent or an alkaline earth metal salt, has a high (6S) content of from, for example, 70 to more than 95%. Contaminating (6R)-folinate can be completely removed from a folinate greatly enriched with the (6S) form in this way by recrystallization. However, if the content of (6S)-folinate is only about 60% or less, recrystallization results in the racemate, the (6R,S) form, being formed again and the excess (6S) form remaining in solution.

The method is straightforward and, when the process is controlled optimally, also very efficient.

Salts of (6R,S)-folinic acid which are particularly suitable as starting materials include but are not limited to the sodium, potassium, calcium, magnesium, strontium or barium salt. The sodium, and in particular, the calcium and magnesium salt are preferred, because these can be used directly as pharmaceutical after resolution, isolation and purification have taken place.

The inorganic or organic acids on which the corresponding salts are based are preferably strong acids, with the organic acids preferably containing 1 to 4 C atoms. Suitable acids include but are not limited to hydriodic acid, hydrobromic acid, hydrochloric acid and nitric acid as inorganic acids and formic acid, lactic acid, citric acid and methanesulfonic acid as organic acids.

Suitable water-soluble alkali metal, ammonium or alkaline earth metal salts which are useful include but are not limited to halides, in particular the iodides and bromides. The following are specifically preferred: sodium iodide, sodium bromide, sodium chloride, potassium iodide, potassium bromide, potassium chloride, ammonium iodide, ammonium bromide, ammonium chloride, calcium iodide, calcium bromide, calcium chloride, magnesium bromide, magnesium chloride, strontium bromide, strontium chloride, barium iodide, barium bromide and barium chloride.

A water-soluble alkaline earth metal salt, preferably calcium iodide, calcium bromide, calcium chloride, magnesium bromide or magnesium chloride, is expediently added to a solution of an alkali metal (6R,S)-folinate.

In addition, the resolution according to the invention can also be performed by the addition of another water-soluble alkali metal, ammonium and alkaline earth metal salts such as, for example, sodium nitrate, potassium nitrate, ammonium nitrate, sodium formate, sodium lactate, sodium citrate, calcium lactate or sodium methanesulfonate. Thus, it is seen that a wide variety of alkali metal, alkaline earth metal, or ammonium salts of organic or inorganic acids can be used to precipitate the 6R Water-miscible organic solvents which are suitable for the isolation of (6S)-folinates include but are not limted to lower alcohols such as methanol, ethanol, n-propanol and isopropanol, glycol ethers such as 2-methoxyethanol, 2-ethoxyethanol, 2-butyloxyethanol, 1-methoxy-2-propanol, 1,2-dimethoxyethane, 1,2-diethoxyethane, as well as dioxane, tetrahydrofuran, lower ketones such as acetone, methyl ethyl ketone, methoxyacetone, 1,3-dimethoxyacetone, plus acetonitrile. Lower alcohols or ketones, especially methanol, ethanol, isopropanol and acetone, are preferred.

For crystallization or recrystallization of the resultant (6S) folinate, suitable water-soluble alkaline earth metal salts for separating out corresponding (6S)-folinates include but are not limited to alkaline earth metal halides such as, for example, calcium chloride, calcium bromide, calcium iodide, magnesium chloride, magnesium bromide, strontium chloride, strontium bromide or a barium halide. Calcium chloride and magnesium chloride are preferred for this purpose.

In a preferred embodiment of the invention a hot aqueous solution of Ca-(6R,S)-folinate is mixed with alkali or ammonium halide, preferably sodium or ammonium bromide, chilled to 20°-25° C., seeded with authentic Ca-(6R)-folinate and chilled to 0°-5° C. The separated Ca-(6R)-folinate is filtered and the filtrate is mixed with calcium chloride after which almost pure Ca-(6S)-folinate separates out slowly.

Accordingly, the invention further comprises using as the alkali metal or alkaline earth metal salt of (6R,S)-folinic acid, preferably the sodium, calcium or magnesium salt, as the water-soluble salt of an inorganic acid, preferably a sodium, potassium or ammonium halide, in particular sodium iodide, sodium bromide, sodium chloride, potassium iodide, potassium bromide, potassium chloride, ammonium iodide, ammonium bromide and/or ammonium chloride, and as the organic solvent for precipitating the corresponding (6S)-folinate preferably a lower alcohol or a lower ketone and/or as water-soluble alkaline earth metal salt a calcium or magnesium halide.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application Swiss Patent Application No. 04 182/88-3, filed Nov. 11, 1988, are hereby incorporated by reference.

EXAMPLES

Example 1

Resolution of calcium(6R,S)-folinate and isolation of calcium(6R)-folinate and of calcium(6S)-folinate 50 g of pure calcium(6R,S)-folinate are dissolved in 500 ml of water, and 100 g of sodium iodide are added. The pH of the solution is adjusted to 7.0. The solution is then cooled to 1° C, while stirring. The pH of the solution rises to about 7.7.

(a) After 15-20 h, the product which has precipitated out is filtered off and washed with concentrated aqueous sodium iodide solution and then with ethanol. Calcium(6R)-folinate with a (6R) content of 98.1% is obtained; determined by HPLC using a chiral column (Resolvosil-BSA- ( 7). Recrystallization from water in the presence of calcium chloride results in pure calcium(6R)-folinate with a (6R) content of 100.0%.

Specific rotation $[\alpha]^{20}_D = +43.7°$ (based on anhydrous Ca salt). Solubility in water: at 20° C.: ]1.7 g/100 ml (b) Ethanol is added to the filtrate, which is cooled to 3° C. while stirring. After 15-20 h, the product which has precipitated out is filtered off and washed with ethanol. Calcium folinate containing 84% calcium(6S)-folinate and 16% calcium(6R)-folinate is obtained. Recrystallization of this from water in the presence of calcium chloride results in calcium(6S)-folinate with a 6S) content of 97.6%. The (6S) content after a further recrystallization is $\geq 99.5\%$.

Specific rotation $[\alpha]^{20}_D = -15°$ C. (based on anhydrous Ca salt.)

EXAMPLE 2

Resolution of (6R,S)-folinic acid and isolation of sodium(6R)-folinate and calcium(6S)-folinate 25 g of (6R,S)-folinic acid are suspended in 70 ml of water and dissolved by adding 49 ml of 2 N sodium hydroxide solution. 40 g of sodium chloride and 140 g of sodium iodide are added to the solution. A gel forms and separates out.

(a) The gel is filtered off after a few hours and washed thoroughly with methanol. Optically pure sodium(6R)-folinate with a (6R) content of 99% is obtained.

(b) 25 g of calcium chloride are added to the mother liquor, and the pH is adjusted to 8.5, after which calcium(6S)-folinate with a (6S) content of 78% gradually separates out. This crude calcium(6S)-folinate is dissolved in water at 30°–35° C., active carbon and a filtration aid (Solkafloc ®) are added, the mixture is filtered and the filtrate is evaporated to a concentration of 10% and left to crystallize at 5° to 1° C. Calcium(6S)folinate with a (6S) content of approximately 98% is obtained.

EXAMPLE 3

Resolution of (6R,S)-folinic acid and isolation of sodium(6R)-folinate and magnesium(6S)-folinate 25 g of (6R,S)-folinic acid are suspended in 75 ml of water and dissolved by addition of 5 N aqueous sodium hydroxide. 75 g of sodium bromide and then 200 ml of methanol are added to the weakly alkaline solution while stirring. After 2 weeks, sodium(6R)-folinate gradually crystallizes out.

(a) The crystallizate is filtered off, washed with methanol and dried. Virtually optically pure sodium(6R)folinate with a (6R) content of 98% is obtained. Specific rotation: $[\alpha]^{20}_D = +39.5°$ (based on anhydrous Na salt, c=1% in water).

(b) Methanol is removed from the mother liquor, the pH is adjusted to 9.8 and 25 g of magnesium chloride are added and the mixture is stirred gently. After some time magnesium(6S)-folinate gradually crystallizes out. After about 100 h it is filtered off, washed thoroughly with ethanol and dried. (6S)-content 85%. Optically pure magnesium(6S)-folinate is obtained by recrystallization in the presence of magnesium chloride.

EXAMPLE 4

Resolution of sodium(6S)-folinate and isolation of the two diastereomers 25 g of (6R,S)-folinic acid are dissolved in 75 ml of water by addition of 5 N aqueous sodium hydroxide, 140 g of sodium iodide are added at 20.C, and the mixture is cooled to 5° C. while stirring.

(a) After standing overnight the sodium(6R)-folinate which has separated out is filtered off and washed with acetone. The resulting product has a (6R) content of 82.9%.

(b) 600 ml of acetone are added to the combined mother liquors, and the mixture is stirred at 0.C. The product which has precipitated out is filtered off. It consists primarily of sodium(6S)-folinate with a (6S) content of 71%.

EXAMPLE 5

Resolution of calcium(6R,S)-folinate by addition of ammonium iodide in approximately neutral medium 50 g of calcium (6R,S)-folinate and 100 g of ammonium iodide are dissolved in 500 ml of water at 36° C. The solution has a pH of 7.7. It is then allowed to cool slowly to room temperature, while stirring, and is further cooled, stirring continuously, to 5.C and finally to 0°–2° C., and the solution is seeded by addition of a few milligrams of pure calcium(6R)-folinate, when crystallization starts.

(a) The product which has crystallized out from this and consists predominantly of calcium(6R)-folinate is filtered off, washed with ethanol and dried. Content of (6R)-folinate: 98%.

(b) The filtrate is combined with the washing solutions and, while stirring, 1 liter of ethanol is also added. The fraction which gradually separates out and consists mainly of calcium(6S)-folinate is filtered off, washed with ethanol and dried. The content of (6S)folinate is 96%. The resulting crude calcium(6R)-folinate and calcium (6S)-folinate are each recrystallized from a little water with addition of active carbon and filtration aid, which raises the content of (6R)- and (6S)-folinate, respectively, to 99.5–99.7%.

EXAMPLE 6

Resolution of calcium(6R,S)-folinate by addition of sodium bromide in approximately neutral medium and subsequent isolation of calcium(6S)-folinate by addition of $CaCl_2$.

75 g of sodium bromide are added to 50 g of calcium(6R,S)-folinate in 500 ml of water. The pH of the solution is 7.4. It is cooled, while stirring, from 35° C. to 1°–3° C., after which slow crystallization starts.

(a) The crystals are filtered off and washed with methanol. The resulting crystals composed of calcium(6R)folinate have a (6R) content of 93%.

(b) 100 g of calcium chloride are added to the filtrate, after which calcium (6S)-folinate precipitates out. It is filtered off and washed with ethanol. The resulting Ca(6S)-folinate has a (6S) content of 84%. Pure calcium(6S)-folinate with a (6S) content of 99.6% is obtained in good yield by recrystallization from a little water in the presence of calcium chloride.

EXAMPLE 7

Resolution of calcium(6R,S)-folinate in approximately neutral medium by addition of ammonium bromide.

70 g of ammonium bromide are added to 50 g of calcium (6R,S)-folinate in 500 ml of water. The pH of the solution is 6.5. The resulting solution is cooled, while stirring, to 0° C. and seeded with authentic Ca(6R)-folinate. Crystallization starts gradually.

(a) After the increase in the Ca(6S) content of the supernatant solution ceases, i.e., no further amounts of Ca(6R)-folinate separate out, filtration and washing with methanol and ethanol are carried out. The resulting Ca(6R)-folinate has a (6R) content of 93.8%.

(b) 100 g of calcium chloride are added to the above filtrate, and the pH is adjusted to 7, after which Ca(6S)-folinate gradually separates out. The resulting product is filtered off and washed with ethanol. The content of Ca(6S)-folinate is 98.7%. Pure Ca(6S)-folinate is obtained from this by recrystallization in the presence of calcium chloride.

EXAMPLE 8

Resolution of calcium(6R,S)-folinate by addition of potassium iodide 500 ml of water and 110 g of potassium iodide are added to 50 g of calcium(6R,S)-folinate, which is dissolved at 55.C. The resulting solution (pH 7.1) is cooled while stirring, stepwise to 0.C and seeded with authentic Ca(6R)-folinate.

(a) After leaving to stand overnight, the crystals which have separated out are filtered off and washed with a little potassium iodide solution and with ethanol. The Ca(6R)-folinate obtained in this way is reasonably pure. The content of (6R) diastereomer is 99.1%.

(b) 100 g of calcium chloride is 50 ml of water are added to the filtrate at 60° C., the pH is adjusted to 7.3 by addition of a little sodium hydroxide, and the solution is cooled stepwise to 15° C., when calcium(6S)-folinate crystallizes out.

After 3 days, the crystals are filtered off and washed with cold calcium chloride solution and with ethanol. The crude calcium(6S)-folinate which is obtained in high yield has (6S) content of 97.3%.

EXAMPLE 9

Resolution of calcium (6R,S)-folinate by addition of sodium chloride 50 g of pure calcium(6R,S)-folinate are dissolved in 320 ml of water at 60° C., 35 g of sodium chloride are added and, while stirring, the mixture is gradually cooled to 0.C and, at the same time, seeded with authentic Ca(6R)-folinate.

(a) The crystals which slowly separate out are filtered off. They consist of crude Ca(6R)-folinate with a (6R) content of 82.5%.

(b) Ca(6S)-folinate is obtained from the filtrate by addition of calcium chloride and ethanol. If the same procedure is carried out but the amount of added sodium chloride is halved to 17.5 g, crude Ca(6R)-folinate with a (6R) content of only just 67% is obtained. Approximately the same result is obtained when, although 35 g of sodium chloride are added, Ca(6R,S)-folinate is used for seeding in place of Ca(6R)-folinate.

EXAMPLE 10

Resolution of 50 g of calcium(6R,S)-folinate in 500 ml of water by addition of 35 g of ammonium chloride in analogy to Example 7

Ca(6R)-folinate with a (6R) content of 92.7% and, after addition of 100 g of calcium chloride to the mother liquor, Ca(6S)-folinate with a (6S) content of 97% are obtained.

EXAMPLE 11

Resolution of 50 g of calcium(6R,S)-folinate by addition of 100 g of tetramethylammonium bromide in 500 ml of water in analogy to Example 7

Ca(6R)-folinate with a (6R) content of 89.1% and Ca(6S)-folinate with a (6S) content of 97.4% are obtained.

EXAMPLE 12

Resolution of 50 g of calcium(6R,S)-folinate in 400 ml of water by addition of about 125 g of diethanolamine hydrobromide in 100 ml of water The following are obtained when the resolution is carried out in analogy to Example 7: Ca(6R)-folinate with a (6R) content of 99.1% and Ca(6S)-folinate with a (6S) content of 80%.

EXAMPLE 13

Resolution with ammonium bromide or ammonium chloride of calcium(6R,S)-folinate obtained in situ from 5,10-methenyltetrahydrofolic acid [5,10-CH-(6R,S)-THF=anhydroleucovorin]

12 6 g of calcium hydroxide are dissolved in 900 ml of water at 90° C. 110 g of anhydroleucovorin bromide hydrobromide ([5,10-CH-(6R,S)-THF]$^{(+)}$Br$^{(-)}$OHBr) are added to the stirred solution within a few minutes and, at the same time, 25% strength aqueous ammonia is added in order to maintain the pH of the reaction solution at 6. The resulting solution is then refluxed at pH 6 for 3–4 hours, during which Ca(6R,S)-folinate (5-CHO-THF) forms.

(a) The reaction solution is clarified by treatment with active carbon and filtration aid, 100 g of ammonium bromide are added, the pH is adjusted to 7, and the solution is cooled and seeded with authentic Ca(6R)-folinate, after which most of the Ca(6R)-folinate gradually separates out. The crystals are filtered off and washed. They have a (6R) content of 98.3%.

(b) 200 g of calcium chloride in 100 g of water are added to the filtrate, the pH is adjusted to 7, and the solution is seeded with authentic Ca(6S)-folinate, after which the Ca(6S)-folinate present crystallizes out. The crystals are filtered off. They have a (6S) content of 92%.

It is also possible in the preceding example to replace anhydroleucovorin bromide hydrobromide by the equivalent amount of anhydroleucovorin chloride hydrochloride and the ammonium bromide by the same amount of ammonium bromide. A similar result is obtained in this case.

The following analogous resolutions are carried out in a manner similar to that described in the preceding examples:

EXAMPLE 14

Resolution of magnesium(6R,S)-folinate into its components by addition of ammonium bromide in approximately neutral medium.

EXAMPLE 15

Resolution of strontium(6R,S)-folinate by addition of sodium iodide, removal of Sr(6R)-folinate and subsequent precipitation out of Sr(6S)-folinate by addition of 2-methoxyethanol and strontium chloride.

EXAMPLE 16

Resolution of barium(6R,S)-folinate and isolation of Ba(6R)-folinate and of Ba(6S)-folinate initially by addition of barium iodide and then of 1,2-dimethoxyethane.

EXAMPLE 17

Resolution of sodium(6R,S)-folinate by addition of magnesium bromide, removal of magnesium(6R)-folinate, addition of calcium chloride to the filtrate and isolation of calcium(6S)-folinate.

EXAMPLE 18

Resolution of calcium(6R,S)-folinate by addition of magnesium bromide, removal of (6R)-folinate which has separated out, addition of calcium chloride to the filtrate and isolation of the calcium(6S)-folinate which separates out in this case.

EXAMPLE 19

Resolution of Ca(6R,S)-folinate by addition of tetraethylammonium bromide.

EXAMPLE 20

Resolution of Ca(6R,S)-folinate by addition of tetrabutylammonium bromide.

EXAMPLE 21

Resolution of Ca(6R,S)-folinate by addition of triethylamine hydrochloride.

EXAMPLE 22

Resolution of Mg(6R,S)-folinate by addition of diethanolamine hydrochloride.

EXAMPLE 23

Resolution of Ca(6R,S)-folinate by addition of benzylamine hydroiodide.

EXAMPLE 24

Resolution of Ca(6R,S)-folinate by addition of morpholine hydrobromide.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of separating diastereomers of (6R,S)-folinates, comprising adding a sufficient amount of a water-soluble alkali metal or ammonium salt of an inorganic or organic acid to an aqueous starting solution of an alkali metal or alkaline earth metal salt of (6R,S)-folinic acid at a neutral pH to precipitate the (6R)-folinate, separating off the resultant (6R)-folinate precipitate and isolating the (6S)-folinate from the filtrate.

2. A method of claim 1, wherein the (6S)-folinate is precipitated out of the filtrate by adding a water-miscible organic solvent, filtering off the resultant (6S)-folinate precipitate and, optionally, recrystallizing the (6S)-folinate.

3. A method of claim 1, wherein the (6S)-folinate is precipitated out of the filtrate by adding a water-soluble alkaline earth metal salt, filtering off the resultant (6S)-folinate precipitate and, optionally, recrystallizing the (6S)-folinate.

4. A method of claim 1, wherein the (6S)-folinate is precipitated out of the filtrate by adding a water-miscible organic solvent and a water-soluble alkaline earth metal salt, filtering off the resultant (6S)-folinate precipitate and, optionally, recrystallizing the (6S)-folinate.

5. A method of claim 1, wherein the alkali metal or alkaline earth metal salt of (6R,S)-folinic acid in the aqueous starting solution is a sodium, calcium or magnesium salt of (6R,S)-folinic acid.

6. A method of claim 5, wherein the metal salt is a calcium salt.

7. A method of claim 5, wherein the metal salt is a magnesium salt.

8. A method of claim 1, wherein a sodium, potassium or ammonium halide is used as the water-soluble alkali metal or ammonium salt of an inorganic acid.

9. A method of claim 8, wherein the sodium, potassium or ammonium halide is selected from the group consisting of sodium iodide, sodium bromide, sodium chloride, potassium iodide, potassium bromide, potassium chloride, ammonium iodide, ammonium bromide and ammonium chloride.

10. A method of claim 2, wherein a lower alcohol or a lower ketone is used as the organic solvent.

11. A method of claim 3, wherein a calcium or magnesium halide is used as the water-soluble alkaline earth metal salt for separating out the (6S)-folinate.

12. A method of claim 4, wherein a calcium or magnesium halide is used as the water-soluble alkaline earth metal salt for separating out the (6S)-folinate.

13. A method for the separation of a (6R)-folinate from its diastereomer, comprising adding a water-soluble alkali metal or ammonium salt of an inorganic or organic acid to an aqueous starting solution of an alkali metal or alkaline earth metal salt of (6R,S)-folinic acid at a neutral pH to precipitate the (6R)-folinate and separating off the resultant (6R)-folinate precipitate.

14. A method for the separation of a (6S)-folinate from its diastereomer, comprising adding a water-soluble alkali metal or ammonium salt of an inorganic or organic acid to an aqueous starting solution of an alkali metal or alkaline earth metal salt of (6R,S)-folinic acid at a neutral pH to precipitate the (6R)-folinate, separating off the resultant (6R)-folinate precipitate and isolating the (6S)-folinate from the filtrate.

15. A method of claim 14, wherein the (6S)-folinate is precipitated out of the filtrate by adding a water-miscible organic solvent, filtering off the resultant (6S)-folinate precipitate and, optionally, recrystallizing the (6S)-folinate.

16. A method of claim 14, wherein the (6S)-folinate is precipitated out of the filtrate by adding a water-soluble alkaline earth metal salt, filtering off the resultant (6S)-folinate precipitate and, optionally, recrystallizing the (6S)-folinate.

17. A method of claim 14, wherein the (6S)-folinate is precipitated out of the filtrate by adding a water-miscible organic solvent and a water-soluble alkaline earth metal salt, filtering off the resultant (6S)-folinate precipitate and, optionally, recrystallizing the (6S)-folinate.

18. A method of claim 3, wherein the alkali metal or ammonium salt of an inorganic or organic acid is an alkali metal or ammonium salt of a hydrohalic acid.

19. A method of claim 18, wherein the hydrohalic acid is hydrobromic acid, hydroiodic acid, or hydrochloric acid.

20. A method of claim 18, wherein the separating off of the resultant alkaline earth (6R)-folinate precipitate is conducted by filtration.

21. A method of claim 1, wherein at least one of the resultant separated diastereomers has a purity of 98-100%.

* * * * *